(12) United States Patent
Heath et al.

(10) Patent No.: US 12,196,729 B1
(45) Date of Patent: Jan. 14, 2025

(54) CHEMICAL WAVE PERTURBATION DETECTION SYSTEMS AND METHODS

(71) Applicant: National Technology & Engineering Solutions of Sandia, LLC, Albuquerque, NM (US)

(72) Inventors: Jason E. Heath, Edgewood, NM (US); Kristopher L. Kuhlman, Albuquerque, NM (US); Thomas A. Dewers, Albuquerque, NM (US); Richard P. Jensen, Albuquerque, NM (US); Jacob A. Harvey, Rio Rancho, NM (US); Robert J. Finch, Albuquerque, NM (US)

(73) Assignee: National Technology & Engineering Solutions of Sandia, LLC, Albuquerque, NM (US)

(*) Notice: Subject to any disclaimer, the term of this patent is extended or adjusted under 35 U.S.C. 154(b) by 491 days.

(21) Appl. No.: 17/691,753

(22) Filed: Mar. 10, 2022

Related U.S. Application Data

(60) Provisional application No. 63/229,760, filed on Aug. 5, 2021, provisional application No. 63/159,100, filed on Mar. 10, 2021.

(51) Int. Cl.
*G01N 33/00* (2006.01)
(52) U.S. Cl.
CPC ................. *G01N 33/0036* (2013.01)
(58) Field of Classification Search
CPC .................................................. G01N 33/0036
USPC .......................................................... 73/23.2
See application file for complete search history.

(56) References Cited

U.S. PATENT DOCUMENTS

2009/0317845 A1* 12/2009 Raguse ............ G01N 33/54373
435/7.94

OTHER PUBLICATIONS

Dateo et al. "Systematic design of chemical oscillators. 5. Bistability and oscillations in the autocatalytic chlorite-iodide reaction in a stirred-flow reactor." Journal of the American Chemical Society 104.2 (1982): 504-509. (Year: 1982).*

(Continued)

*Primary Examiner* — Walter L Lindsay, Jr.
*Assistant Examiner* — Philip T Fadul
(74) *Attorney, Agent, or Firm* — Daniel J. Jenkins

(57) ABSTRACT

Chemical wave systems that utilize chemical compounds with nonlinear chemical wave behavior can be used to detect or sense material changes such as a change in a radiation source. Such chemical systems include autocatalysis that produce self-sustaining spatial and/or temporal fluctuations in chemical attributes such as species concentrations, pH, and/or redox state. Through application of the chemical compounds with wave behavior into engineered geologic environments, such as those for containment of a liquid or solid, the chemical wave behavior may be triggered or modified by perturbations, including intrusion into the environment. The chemical wave behavior is an indicator of the said perturbation and monitored by various means tailored to the type of chemical waves. The chemical waves can have a type of "fingerprint" based on their wave behavior that lasts beyond a transient disturbance that could later be discerned by measurement of the chemical wave attributes.

13 Claims, 8 Drawing Sheets

(56) References Cited

OTHER PUBLICATIONS

Safety of Spent Fuel Storage, U.S. Nuclear Regulatory Commission, Apr. 2017, NUREG/BR-0528, 16 pages.
Burkholder, J. B. et al., "Chemical Kinetics and Photochemical Data for Use in Atmospheric Studies," Jet Propulsion Laboratory, Oct. 2015, 1392 pages.
Gerasimov, G. Y., "Radiation-Chemical Formation of Ozone in an Oxygen-Containing Gas Atmosphere," High Energy Chemistry (2004) 38(2):75-80, translated from Khimiya Vysokikh Energii (2004) 38(2):101-106.
Morco, R. P., "Gamma-Radiolysis Kinetics and Its Role in the Overall Dynamics of Materials Degradation," Electronic Thesis and Dissertation Repository (2020) The University of Western Ontario, 271 pages.
Orbán, M. et al., pH-Regulated Chemical Oscillators, Accounts of Chemical Research (2015) 48:593-601.
Szalai, I. et al., "Mechanistic studies on the bromate-1,4-cyclohexanedione-ferroin oscillatory system," Phys. Chem. Chem. Phys. (2002) 4:1271-1275.
Vodopivec, D. M. E., "Hydrodynamic Instabilities Coupled with Complex Chemical Reactions: Control, Characterization, and Their Modeling," Ph.D Dissertation, Universidade de Santiago de Compostela (2020) 303 pages.
Wittman, R., "Radiolysis Model Sensitivity Analysis for a Used Fuel Storage Canister," Used Fuel Disposition Campaign, U.S. DOE, Sep. 20, 2013, PNNL-22773, 62 pages.

\* cited by examiner

CHEMICAL WAVE PERTURBATION DETECTION SYSTEMS AND METHODS

RELATED APPLICATIONS

This application claims priority to U.S. Provisional Patent Application No. 63/159,100, filed on Mar. 10, 2021, entitled "CHEMICAL WAVE MONITORING SYSTEMS AND METHODS," and to U.S. Provisional Patent Application No. 63/229,760, filed on Aug. 5, 2021, entitled "CHEMICAL WAVE PERTURBATION DETECTOR SYSTEMS AND METHODS FOR ENGINEERED GEOENVIROMENTS," the entireties of which are incorporated herein by reference in their entireties.

STATEMENT OF GOVERNMENT INTEREST

The United States Government has rights in this invention pursuant to Contract No. DE-NA0003525 between the United State Department of Energy and National Technology & Engineering Solutions of Sandia, LLC, both for the operation of the Sandia National Laboratories.

FIELD

The present disclosure is generally directed to systems and methods for sensing, signal amplification, analysis, surveillance, and/or perturbation-intrusion detection using nonlinear chemical waves.

BACKGROUND

The sensing of stimuli including changes or perturbations in spatial and chemical properties is an important operation in monitoring of many applications in spaces that may be hazardous or impossible to access using conventional remote sensing, sensors, and/or information transmission systems. For example, in chemically reactive or radioactive environments, sensor life may be severely limited due to heat, corrosive, and/or radiation degradation. In other examples, it may be impractical to place sensors and/or transmit information from remote locations simply due to inaccessibility in systems that require sealed containment or inherently have confined spaces.

Temporary or permanent storage or disposal of gases, liquids, and/or solids, including waste material, in engineered subsurface geologic environments may require confirmation that stored materials have not been disturbed or removed by unauthorized human activities or other unplanned processes. For nuclear waste repositories, an extended operational period may exist between when the first waste container is emplaced in a mined geological repository and when the access to the repository is completely sealed, up to several decades later. Depending on the design of the repository (i.e., emplacement of intermediate drift seals or bulkheads), the waste may be difficult to routinely access for inspection to ensure that leakage, unauthorized access, and/or removal of waste has not occurred, and thus the geo-repository may be potentially vulnerable to proliferation until the final closure of the repository is complete.

What is needed are systems and methods that can be added to environments such as chemical processing or storage facilities with physically difficult-to-access spaces, to perform sensing, surveillance, and/or perturbation or intrusion detection and methods that overcome the limitations of the prior art.

SUMMARY OF THE DISCLOSURE

Figures 1A, 1B:
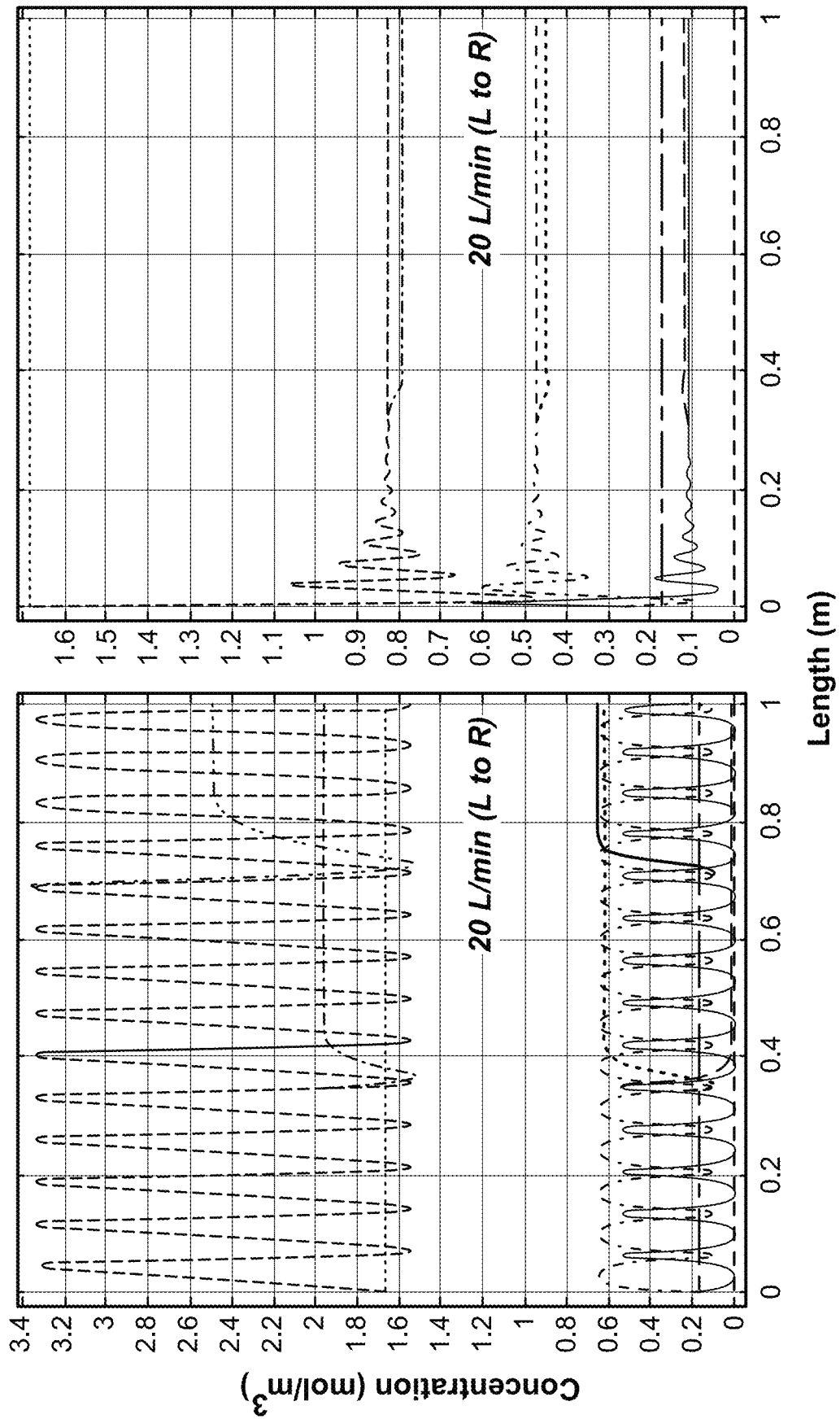
FIG. 1A illustrates propagating chemical waves in $O_x$—$HO_x$ air systems showing rapid, large amplitude waves developing from left to right in a one-dimensional injection model at a fast rate of 20 L/min.
FIG. 1B illustrates the same system as FIG. 1A but exposed to a high dose of gamma radiation of 1 Gy/hr, which suppresses the oscillations.

The present disclosure is directed to non-linear chemical wave systems and their behaviors that provide information transmission, amplification of chemical signatures, perturbation detection, intrusion detection, and/or chemical/radiological sensing, surveillance, and detection, collectively referred to as monitoring or geospatial sensing. In an embodiment, the chemical wave systems are used in engineered geologic environments that involve storage or containment of nuclear waste materials. Nuclear waste storage is used as an illustrative example, but the information in this disclosure can apply to the detection of other types of materials that can chemically or radiologically perturbate a chemical system, the chemical system being a sensing backbone of the storage system. Chemical processing facilities are an example of another type of system that may have difficult-to-access spaces that require monitoring. The chemical system(s) and methods described herein are suited to monitor physically difficult-to-access environments.

The present disclosure is further directed to a suite of chemical compounds applied into or found in an aqueous and/or gaseous environment. The chemical compounds have nonlinear behavior arising from interdependent (or coupled) reaction kinetics involved in photolytic, radiolytic, and speciation reactions involving gas- or liquid-phase chemical species exposed to conditions far from chemical equilibrium. In other words, the chemical compounds may show a cyclic or autocatalytic behavior that produces self-sustaining spatial and/or temporal fluctuations in chemical attributes such as species concentrations, pH, and/or redox state. For example, in air environments exposed to ultraviolet radiation, this behavior may involve so-called chemical radicals of oxygen and air constituents induced through photolytic reaction schemes. Far from equilibrium conditions can be induced by, but are not limited to, the following: sunlight, various forms of radiation, changes in thermal conditions, chemical spills, leakage from storage containers, intrusions into storage environments, and presence of metastable chemical conditions or constituents. Temporal fluctuations can involve a cyclic or oscillatory behavior; spatial fluctuations result in sustaining chemical fluctuations that propagate through space, known as chemical waves. Through application of the chemical compounds with wave behavior into engineered geologic environments, such as those for containment of a liquid or solid, the chemical wave behavior may be triggered or modified by perturbations, including intrusion into the environment and other far-from equilibrium conditions. The chemical wave behavior is an indicator of the said perturbation and monitored by various means tailored to the type of chemical waves. The chemical waves can have a type of "fingerprint" (e.g., in the phase space or concentration portrait on key oscillating species, constituents, or attributes) based on their wave behavior that lasts beyond a transient disturbance that could later be discerned by measurement of the chemical wave attributes.

Nonlinear chemical waves are self-sustaining compositional variances that can propagate over distances without attenuation. Owing to their nonlinear nature, they commonly exhibit excitability to environmental perturbations, can exhibit bi-stability, or can propagate as solitary waves or solitons. It is their ability to respond to environmental perturbations and propagate information that renders these systems amenable to development as combined sensing and chemical communication systems. As disclosed herein, chemical waves along with logic tree analysis and/or interpretation methods such as parameter estimation and inverse modeling or interpretation of phase space portraits are used as nonlinear sensors for geospatial applications. Autocatalytic reaction schemes are disclosed that form the prerequisite for developing chemical waves in aqueous and gaseous systems.

Physically difficult-to-access systems may manifest from inherent hazards including radiation sources, heat, chemical reactivity, and/or geometric configurations that prevent emitted and/or reflected signals from the target of interest. Geometric configurations may also result in narrow-to-confined spaces and/or falling hazards. The chemical wave systems of the present disclosure can be space-filling to reach regions and/or components of a system that are otherwise inaccessible. The space-filling capability then allows the chemical wave systems to contact, respond to, amplify, and transmit information out of the inaccessible region to where chemical property read-out of the chemical wave may occur. Thus, the chemical wave systems provide monitoring of difficult-to-access spaces.

According to an embodiment of the disclosure, a monitoring method is disclosed that includes: introducing an autocatalytic chemical wave compound into an area of interest for a first period of time; monitoring the chemical wave compound concentration at one or more detection sites to create a chemical wave profile over the first period of time; and analyzing the monitored chemical wave profiles using inverse modeling and Bayesian parameter estimation to determine if a perturbation has taken place in the second period of time by a perturbation source. The measured chemical wave is used to estimate underlying system state parameters that affect the chemical waves, including substances such as radiation by-products and their locations, type, and strength.

An advantage of the present disclosure is that application of chemical wave systems enables monitoring chemical, radiological and environmental conditions that otherwise may be inaccessible or very difficult to monitor in engineered geological environments, chemical processing facilities, warehouses, or similar facilities.

Another advantage of the present disclosure is that application of chemical wave systems enables monitoring chemical, radiological, and environmental conditions in a hostile environment. For example, a hostile environment may be, but is not limited to a radioactive environment, a chemically corrosive and/or reactive environment, an asphyxiating environment, or an environment where direct human inspection is restricted or otherwise difficult to achieve.

Another advantage of the present disclosure is that chemical wave systems are sensitive to physical changes in an environment such as may indicate movement of sensitive inventory items or physical locations of storage containers. Chemical wave indicators are thus potential indicators of unintentional or intentional tampering, intrusion, breakage of seals, or other unwanted behavior in a storage environment.

Another advantage is that the chemical wave systems, through non-linear feedback reactions, can lead to enhancements or unbounded growth (within a range) in small chemical signals or concentrations that are easier to detect than the target monitored substance or event itself in the system, thereby causing an amplification and improved detection of the target substance or perturbing source.

Another advantage is that chemical wave transmission can propagate against advection, thus offering chemical wave read-out not only downstream but upstream in a host medium with advective flows.

DETAILED DESCRIPTION OF THE DISCLOSURE

Chemical waves are self-sustaining fluctuations in chemical concentrations, speciation, or oxidation state that arise from nonlinear coupling of transport and chemical reactions. Chemical waves respond to and retain a history of encountered stimuli, and the waves propagate spatially even in the absence of advection. Chemical waves can be triggered by trace quantities of solid, gaseous, or liquid chemical compounds, physico-acoustic perturbations, radiation, magnetic fields, thermal changes, and optical/UV stimulation.

The invention's approach introduces chemical wave compounds into existing or introduced fluids and monitors disturbances and/or changes of/or to those chemical wave compounds at a monitored location. The chemical waves can be tailored to perform material accountancy, verification of containment, intrusion detection, and/or surveillance. As used herein, the term "fluids" includes liquids, gels, gases and aerosols. The applied chemical compounds sense characteristics of a host medium by producing diagnostic spatial and temporal patterns in chemical waves as triggered by what is in the host medium that is contacted by the chemicals. The chemical waves perform in situ analysis at different levels of complexity depending on the particular system and application, which may include: identification of particular substances or configurations of items in the host medium; verification that seals or other features have not been damaged or removed; verification that containers have not leaked a substance of interest; counting of items; surveillance of unauthorized intrusion such as by an initial baseline chemical wave application that produces a "template" pattern of chemical waves that is compared to subsequent chemical wave applications whose differences in patterns would confirm an intrusion; logic-tree analysis by utilizing the chemical waves as a chemical circuit whose patterns represents a cascading sequence of logical steps linked to questions about the system of interest; and parameter estimation and inverse modeling of chemical wave information collected from the system to distinguish and characterize system configurations that affect chemical wave behavior.

Data transmission occurs through the propagation of chemical waves within the underlying fluids that have pervaded the host medium, including locations that are difficult to access by other means. The chemical waves encode characteristics of the sensed quantities in their frequencies, amplitudes, and spatial patterns. The chemical waves propagate at velocities controlled by the dynamics and kinetics of the underlying chemical reactions and are modified by transport (i.e., advection/diffusion/dispersion) in the host medium. Chemical wave transmission can propagate against advection, thus offering chemical wave read-out not only downstream but upstream in host medium with advective flows.

Information read-out of the chemical waves is performed by measurement of varying chemical concentrations or states, which may be performed at point locations or integrated along a measurement path, and which may be at different temporal resolutions, such as in real-time or by sampling with later laboratory analysis. Depending on the application, read-out may involve: laser, absorption, and/or vibrational spectroscopy; devices that emit electromagnetic radiation that is absorbed by chemical species of interest as monitored by photo-detection (e.g., photo-diodes or a charged-coupled device (CCD) camera); or lab-based chromatography, spectroscopy, and/or mass spectrometry. For difficult-to-access host media such as a building with hazardous materials, laser-based spectroscopy with beam positioning by mirrors, beam-splitters, and detectors enables precision positioning for measurements and ultimately defines the reachability region of measurements. The chemical waves themselves may propagate information out of regions that are otherwise inaccessible or difficult-to-access to where measurements could be made.

Interpretations of chemical waves are facilitated by understanding what triggers and controls the patterns of the chemical waves. A logic-tree framework is an approach of the invention that maps chemical responses to triggers and their cascading spatial patterns, which is interpreted as a set of inter-related yes/no questions of an event tree analysis. Thus, read-out would give the final results of the logic tree analysis that is performed in situ by the chemical waves themselves. Another interpretational approach of the invention is inverse modeling with coupled computational fluid dynamics and parameter estimation to infer the underlying triggers in the host media that produced the measured chemical waves. Parameter estimation and inverse modeling could be used, for example, to: locate and characterize a target source compound that is perturbing applied chemical waves; or indicate the removal of a substance that would have interacted with the applied chemical wave compounds.

Applications for this chemical wave detecting, sensing, information processing and data transmitter system are diverse and include, but are not limited to, the following scenarios: identification of trace compounds in the host environment (e.g., on floors, walls, or the surfaces or insides of containers); seals or feature evaluation that allows determination if something has been disturbed, such as a container or door; identification of substances that leaked from a container or confinement region; counting of items by chemical wave products accumulating in proportion to interactions with the target item; connectivity assessment of tortuous pathways in a geometrically complex system; and logic tree analysis through chemical wave logic circuits answering a linked set of yes/no questions, which may encompass many of the aforementioned scenarios. These scenarios can be embodied in a variety of industries, research settings, or similar avenues, such as: nuclear safeguards assessment such as those performed by the International Atomic Energy Agency (IAEA) for material accountancy, seal verification, surveillance, and intrusion detection in settings such as spent fuel storage in dry casks, spent fuel storage in pools, or underground nuclear waste disposal; inventory in large warehouses that involve geometrically complex packing with physically difficult-to-access regions—that is, by human, robot, or other agents—such as small or narrow-to-confined spaces, enclosed spaces, or other hazardous spaces with thermal, radiological, chemical and/or other hostile attributes; piping systems for chemical processing or reactors that may involve geometric complexity and features that need monitoring/sensing; subsurface systems that involve natural or induced fracturing such as enhanced geothermal systems where the connectivity is key to thermal profiles and performance; and surficial out-of-doors applications involving leakage in pipelines or other transmission systems as might occur in the investigation of fugitive methane or other contaminant leakage.

The chemical compounds may include but are not limited to gaseous, single or multiphase liquid(s), and/or aerosol-based chemical wave systems. The chemical reactions and/or compounds of chemical wave systems that can exhibit the desired attributes for sensing, analysis, and data transmission are the following (note that these are meant to be representative of classes of similar chemical wave systems and thus similar systems are covered by this invention): iodate, Belousov-Zhabotinsky, and pH chemical oscillators for aqueous systems; photolytic-based chemical oscillators for gaseous systems which involve ozone, $NO_x$ compounds and other common constituents of air and polluted air commonly known as smog; and ozone-halogen chemical oscillators involving liquid droplets and the gas phase for gaseous/aerosol systems.

According to an embodiment of the invention, a chemical wave system or chemosensor using nonlinear chemical reaction networks is used to sense or detect, with an extremely high detection efficiency, a change in radiation presence without a well detector. As the chemical wave system is applied in the host medium's fluid phase (e.g., air or water), the chemical wave system surrounds the to-be-detected target compound or system component. The system can perform a far-field detection of alpha and beta decay from radiological material and can detect radiological materials that emit gamma radiation in physically difficult-to-access locations. The chemical wave systems disclosed in this embodiment can be gas systems or liquid systems and both will be discussed in separate sections below after a general discussion of the chemical wave systems for radiation monitoring.

International Nuclear Safeguards has the objective to prevent diversion of nuclear material to nonpeaceful use including detection, deterrence, and verification. Detection and verification include material accountancy, containment and surveillance, and environmental sampling. Around the globe, dry cask storage of spent nuclear waste is becoming increasingly important as pool storage on site at reactors has limited space, and movement of casks can be problematic. Deep borehole disposal is being explored as a viable option to spent fuel permanent storage, as an alternative to underground mined repositories. Both of these settings pose some unique Safeguards challenges that include poor accessibility. Spent fuel housed in large, heavy casks with radiation, heat, and potentially narrow-to-confined space hazards present difficult and dangerous conditions for verifying seals or detecting potential material diversion. Underground nuclear waste disposal involves making the materials permanently inaccessible, which clearly also makes intrusion detection difficult during emplacement and post emplacement. As discussed herein, we propose chemical wave systems and other chemosensor system concepts as particularly suited for these difficult-to-access systems.

Chemical wave chemosensor systems offer several beneficial components for material accountancy, surveillance-monitoring, and containment verification. Dry cask storage of spent fuel, either in open areas or in "warehouse"-like environments, are examples of appropriate or commensurate environments for application of the chemosensor system. Spent fuel housed in large, heavy casks (e.g., 14-ft long and 150 tons; US Nuclear Regulatory Commission. 2017. Safety of spent fuel storage. NUREG/BR-0528, 16 p.)—with radiation, heat, and potentially narrow-to-confined space and falling hazards—presents conditions that can make it difficult to verify seals or detect potential material diversion. Although these examples of containment vary in size and geometry, a few generalities can be made, including:

- difficulty in verifying seals;
- problems in accessibility (i.e., by cranes or hoists);
- "as low as reasonably achievable" or ALARA issues with exposure and dosing-out hazards; and
- the large number of casks at any given site and the arduous nature of checking many seals.

The chemical wave chemosensor concept surmounts these issues from the perspective of monitoring. A gaseous or gaseous-aerosol chemical wave system is fully space filling, driven by advective-diffusive transport processes. The precise non-linear/autocatalytic chemical system can be engineered to be stimulated by chemical perturbations that exist in the gaseous space (such as ionized air and associated byproducts) or on surfaces (examples include powder residues or chemicals that could be released by seal breaching), or even moved or missing casks (by comparing chemical wave responses over time). A localized excitation of the nonlinear chemical wave system can be distinguishable by the precise perturbation, and the wave motion propagates or broadcasts this messaging through space. With a proper spatial detection system, such as laser spectroscopy or optical methods, the associated excited signals can thus be remotely sensed. Above-ground or subsurface storage of nuclear waste offers ideal systems for application of the chemosensor system. The chemosensor system may enable a type of "everywhere-at-once" pervasive evaluation of a location filled with the chemical waves. Seals themselves or even applied coatings on casks or other parts of the given system could be designed to be particularly sensitive to damage or disturbances from unauthorized activities of concern, which could then broadcast information of tampering when contacted by the chemical wave chemosensors.

Furthermore, permanent disposal of nuclear waste in a mined deep geological repository is considered the most viable option for dealing with legacy radioactive waste from nuclear power generation. Deep geological disposal isolates the waste from the accessible environment for long periods of time, until the waste is safe through radioactive decay. Isolation of radioactive waste in deep boreholes (~3 to 5 km) has also been proposed but has not yet seen the same significant level of investment from countries around the world as deep geologic repositories. An extended operational period will exist between when the first container waste is emplaced in a mined geological repository and when the access to the repository is completely sealed, up to several decades. Depending on the design of the repository (i.e., emplacement of intermediate drift seals or bulkheads), the waste may be difficult to routinely access for inspection, but still vulnerable to proliferation until the final closure of the repository is complete. Chemosensors can be used in components of a generic repository farther from the waste package, in the buffer and/or backfill. These sites could be a target for chemosensor systems since they are engineered systems (i.e., they are often man-made or modified materials designed to serve a specific engineering purpose). As buffers and backfills are usually added immediately after waste emplacement and could be enhanced with additional introduced materials with specific characteristics, they would be a good candidate target for using liquid or gaseous chemosensor systems.

The excavation disturbed zone (EDZ) is a major component in a generic disposal system. This region is a halo of damaged host rock surrounding all the drifts, tunnels, and mine workings. The redistribution of stress around an opening in the subsurface leads to an EDZ, consisting of fractures and damage in the otherwise low-permeability host rocks that can allow rapid flow and transport of gases or liquids adjacent to the excavations. Since the EDZ will surround all the waste packages and is a potentially connected pathway between all parts of the repository, it would be an excellent candidate for the chemosensor system, especially for monitoring and intrusion detection. In an embodiment, the EDZ can be seeded with a solid, liquid, or gaseous component that could be used to sustain a chemosensor system. The chemosensor system in the EDZ has the possibility to transition from Safeguards monitoring for intrusion to being a component of the long-term monitoring network emplaced to monitor the long-term environmental safety performance of the repository (i.e., disposal system performance assessment). Deep borehole disposal has been proposed as a complement to mined repositories for certain shapes and sizes of radioactive waste. Deep boreholes involve emplacing waste deep (~3 to 5 km) into a liquid-filled borehole in low-permeability basement rock. Unlike in a mined repository with relatively easy access for people, liquid-filled boreholes are harder to perform typical accountability. Deep boreholes have an EDZ surrounding them, which might allow application of chemosensors. Thus, there are several potential application spaces for chemosensor systems in deep geological repositories or deep boreholes.

Sensing in Gas Phase Systems with Chemical Waves

The chemical systems use so-called "chemosensors" that operate in background air. In an embodiment, the chemosensor system may include ozone, a strong oxidant, which couples extensively to oxidation-reduction reactions, and is sensitive to UV light, radiation sources, and electrical discharge among other forms of catalysis.

The chemical wave is initially measured as a baseline at one or more positions in the area of interest. The chemical wave is periodically or at a predetermined time measured to determine if a perturbation of the chemical wave is observed. The perturbation can be extrapolated to an activity in the area of interest, such as, but not limited to a radiation leak or change in the radiation profile of the area of interest as analyzed by the mechanisms described herein. Indicators of a detected perturbation, such as leakage, tampered seal, or moved inventory, are observed through a direct variation in behavior of the chemical wave system, such as dampened oscillation, change in wave amplitude or period, or absence of wave behavior. Inverse modeling involving computational fluid dynamics coupled to the set of non-linear/autocatalytic chemical reactions and parameter estimation can be employed to infer the system attributes that affect chemical wave spatial patterns, which can potentially be used to locate substances or events in the host media that affect the measured chemical waves. Inverse modeling and Bayesian parameter estimation can be improved by an initial baseline measurement but can also be performed on measured chemical waves without a baseline to estimate the underlying system state parameters that affect the chemical waves, including substances such as radiation by-products and their locations, type, and strength/fluence.

A simple example of chemical wave behavior is the two-step process of ozone formation in air involving dissociation of molecular oxygen from electron collisions along with the direct formation of ozone via the Chapman reaction (a three-body reaction where the 'M' indicates O, $O_2$, $O_3$, and/or $N_2$). In the $O_x$—$OH_x$ system, under certain UV and radiolytic conditions, this may form a cyclic or autocatalytic production of radical oxygen (O) via the following reactions:

$$e+O_2 \rightarrow O+O+e$$

$$O+O_2+M \rightarrow O_3+M$$

In other embodiments, the chemosensor may be $N_2$ and $NO_x$ (x=0, 1, 2), water vapor, halogen aerosols, and CO and $CO_2$ that also exhibit autocatalysis. The reaction system representing the photolytic, bimolecular, and termolecular reactions in the $O_x$—$OH_x$ system is shown in FIG. 1. It shows how autocatalysis arising from the interdependent reaction kinetics leads to the development of self-propagating chemical waves and how these waves are perturbed by ionizing radiation. For example, the radiation chemical yield of ozone due to air ionizing gamma radiation is ~6.5 molecules/100 eV for a neutron and photon source.

As can be seen in FIG. 1, the evolution of this system involves ozone synthesis and decomposition in a meter-long domain initially devoid of oxygen. This 1D domain is modeled as is commonly done in atmospheric chemistry experimental studies involving a flow tube, which is discussed in more detail below. The chemical system includes $O_2$, oxygen radicals $O(^1D)$ and $O(_3P)$, ozone ($O_3$), and the $HO_x$ species H, $HO_2$, $H_2O_2$, $H_2O$, and OH, which participate in 30 photolytic, bimolecular, and termolecular reactions in air. Rate coefficients for the reactions are taken from Burkholder et al. (2015) (Burkholder, J. B., Sander, S. P., Abbatt, J., Barker, J. R., Huie, R. E., Kolb, C. E., Kurylo, M. J., Orkin, V. L., Wilmouth, D. M., and Wine, P. H., 2015, Chemical Kinetics and Photochemical Data for Use in Atmospheric Studies, Evaluation No. 18, JPL Publication 15-10, Propulsion Laboratory, Pasadena, accessed Nov. 1, 2021, http://jpldataeval.jpl.nasa.gov), and radiolytic reaction rates are estimated from Gerasimov (2004) (Gerasimov, G. Ya., 2004, Radiation-chemical formation of ozone in an oxygen-containing gas atmosphere. High Energy Chemistry 38, 75-80. Translated from Khimiya Vysokikh Energii, Vol. 38, No. 2, 2004, pp. 101-106.). In FIG. 1A, an $O_3$-$O_2$ mixture is introduced from the left of the domain at 20 liters per minute (L/min, laminar flow), and we observe a standing oscillatory wave region system, most evident in the $O_2$ concentration profiles, which expands towards the system outlet on the right. Decreasing the flow rate to 2 L/min results in a propagating chemical wave from left to right (shown are profiles after 30 s increments), and dropping the flow rate another order of magnitude results in a bulk oscillation, past a 0.2 m inlet region. Thus, by varying the flow rate of the 1D system, a range of behaviors was observed, which suggests a range of conditions for testing this system experimentally (discussed below).

Exposing the system to two levels of gamma radiation at the 20 L/min influx rate results in entirely different modes of behavior (FIG. 1B). Low rates of exposure yield a faster oscillation and smaller wavelength of the $O_2$ oscillations (not shown), but higher rates of exposure show a dampening of the nonlinear, oscillatory behavior (FIG. 1B).

In this exemplary embodiment, ozone and other constituents of the $O_x$—$OH_x$—$NO_x$—$CO_x$ gas-phase system are introduced into the area of interest and diffuse or travel across the area of interest to one or more sensors that measure the concentration of chemical constituents at that predetermined location. The changes in concentration of ozone and other constituents can be in the form of localized maxima and minima in concentration that move across the area in traveling waveforms or can appear as a standing wave, even in the presence of advection of air. The period and amplitude of the waveforms are engineered to be sensitive to radiation, chemical leaks, changes in position of storage entities, and tampered seals. In an embodiment, one or more sensors may be included at one or more positions around the area of interest to measure changes in amplitude and/or wavelength. In other embodiments, one or more sensors may be positioned in the area of interest to measure the amount, quantity, or concentration of constituents at those positions. In an embodiment, the sensors may include ozone detectors, chemical compound concentration measurement systems such as, but not limited to carbon monoxide or other gas-phase analyzers, lasers, and/or optical cameras. In an embodiment, the applied chemical wave compounds in the ambient air produce chemical waves that when perturbed can propagate in the general space of the environment and difficult-to-access regions via diffusive transport and not necessarily accompanying air advection. In an embodiment, chemical waves also have the potential to travel upstream against advection, thus providing an opportunity for monitoring upstream and downstream as opposed to only downstream like typical sweep gas operations.

Chemical constituents are introduced into the area of interest so as to have a concentration of between 1 part per billion and 1 part per million. In an embodiment, the ozone concentration in the area of interest may range from 100 to 200 parts per billion as dictated by the propagating chemical wave behavior. The analysis of the ozone concentration is performed by a processor that receives data from the sensors and processes that data to determine the chemical wave profile and to determine the activity associated from the chemical wave measurements.

The area of interest may be open such as exists in many dry cask storage environments or confined fully or partially. In an embodiment, the area of interest may be a room, subterranean space, excavated cavern, warehouse, piping systems, or the like.

The determination of the activity is performed by generating a background response in the environment of concern at an initial date. The analysis is then continued by inspectors or analysts at later times to discern changes from the initial, background state. The nature of any difference between the earlier and later times of analysis are determined by said logic tree analysis, inverse modeling and parameter estimation, or other analytical approaches as are appropriate to the environment. An example is the movement of a dry cask storage container between the initial background measurement and a measurement after a cask has been moved. The movement is detected by the behavior of the chemical wave system and is discerned by the subsequent analytical method.

The determination of the activity may also be performed without an initial baseline. Inverse modeling with computational fluid dynamics coupled to the set of non-linear/autocatalytic chemical reactions and parameter estimation can be used to estimate system attributes that affect chemical wave spatial patterns, such as for scenarios involving a canister that has been breached and leaked material—the material may affect the chemical waves which in turn affects what is measured spatially and input into the inverse modeling and parameter estimation scheme. The inverse modeling may then indicate the location and other attributes such as the type of material, the strength/fluence, and pattern of breaching (e.g., localized or broad). Inverse modeling and Bayesian parameter estimation can continue to input measured data to shift estimates of system attributes over time to track possible changes to the system. Another analysis for determination of activity can include interpretation of the chemical patterns of chemical wave attributes via the phase portraits and how they evolve, as the phase portrait behavior may be diagnostic of system attributes.

Photolysis and Radiolysis Model Verification and Validation

Figure 2B:
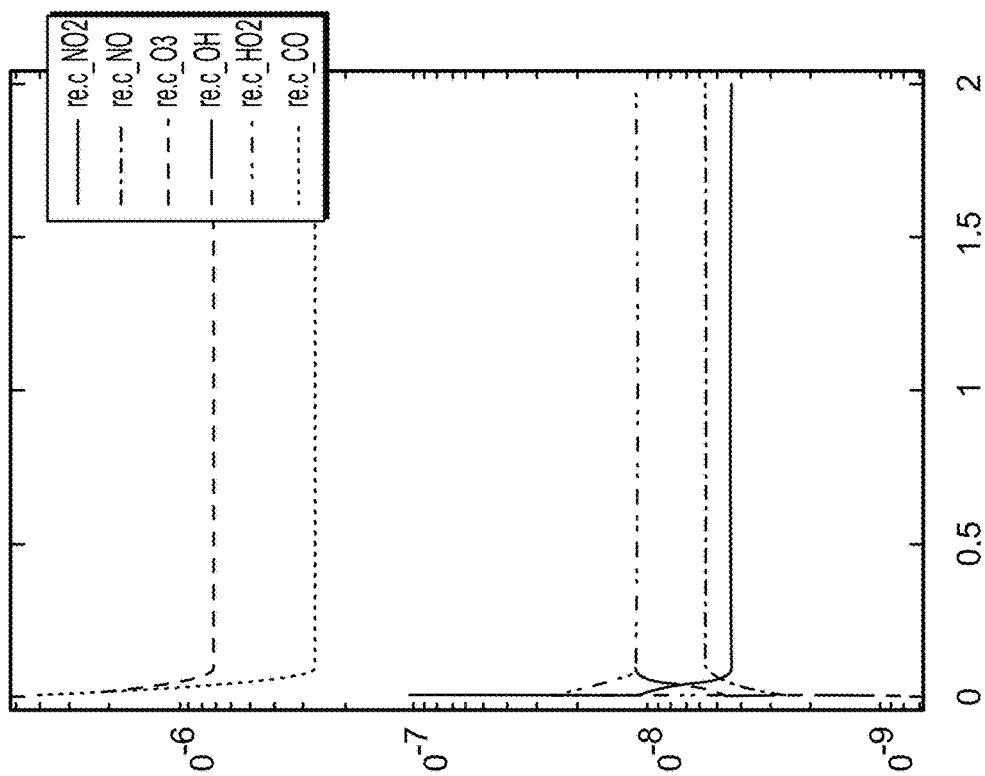
FIG. 2B shows the same system as FIG. 2A but perturbed by gamma radiation. Kinetics follow the laboratory results for a $^{60}$Co source measured through glass for ozone generation in flowing air.
Figure 2A:
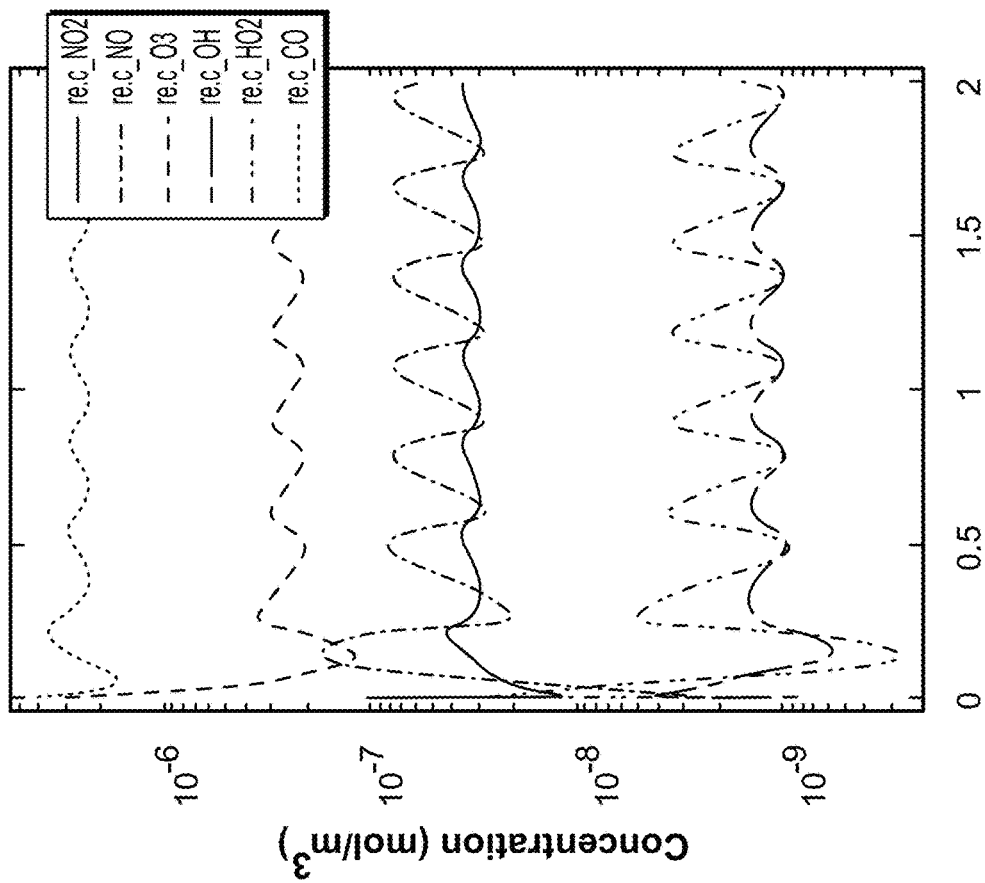
FIG. 2A shows the nonlinear oscillatory behavior in the $O_x$—$OH_x$—$CO_x$—$NO_x$ gas-phase system for a CSTR system with reactor feed at a rate of 2 L/min. Under these conditions (including inlet concentrations) the system displays oscillations with period of ~six hours.

A numerical model for atmospheric bimolecular and termolecular collisions, UV photolysis, and radiolysis kinetics was developed to aid in the design of the gas-phase system. FIG. 2 shows a model of a continuously stirred tank reactor (CSTR) system that can be employed at benchtop scale with compositions of constituents of concern (e.g., ozone, CO, $NO_x$) at levels that pose no hazards associated with reactor effluent into air, with use of a fume hood to vent reactor effluent under normal hood air flow. Exposure to UV radiation with wavelengths in the range of 250 to 350 nm show well developed temporal oscillations with a period of approximately six hours, which is amenable to lab monitoring methods (FIG. 2A). Under exposure to air ionization at relatively high dose rate of 1 Gy/hr, FIG. 2B shows that the ionization products quench the oscillatory behavior, demonstrating a sensitivity of the chemical wave system to a radiation source.

This model suggests the design in FIG. 2, for the CSTR that involves: a source for clean dry air; sources of additional $CO_x$, $NO_x$, and $O_3$ (using a generator that uses air and $NO_2$ canisters as sources); a gas mixing manifold; a source for humidity (a simple heated flask with water, or using salt mixtures); a central chamber with UV sources of varying wavelengths; and gas analyzers attached to the CSTR effluent side.

The numerical model we are using in this context is based on the humid air radiolysis model of Wittman (2013) (Wittman, R., 2013, Radiolysis model sensitivity for a Used Fuel Storage Canister, Pacific Northwest National Laboratories PNNL-22773, 48p.), which uses a simplified residence time model to simulate transport and couples bimolecular and termolecular atmospheric reactions with radiolysis terms, for 40 gas-phase species.

Figure 3:
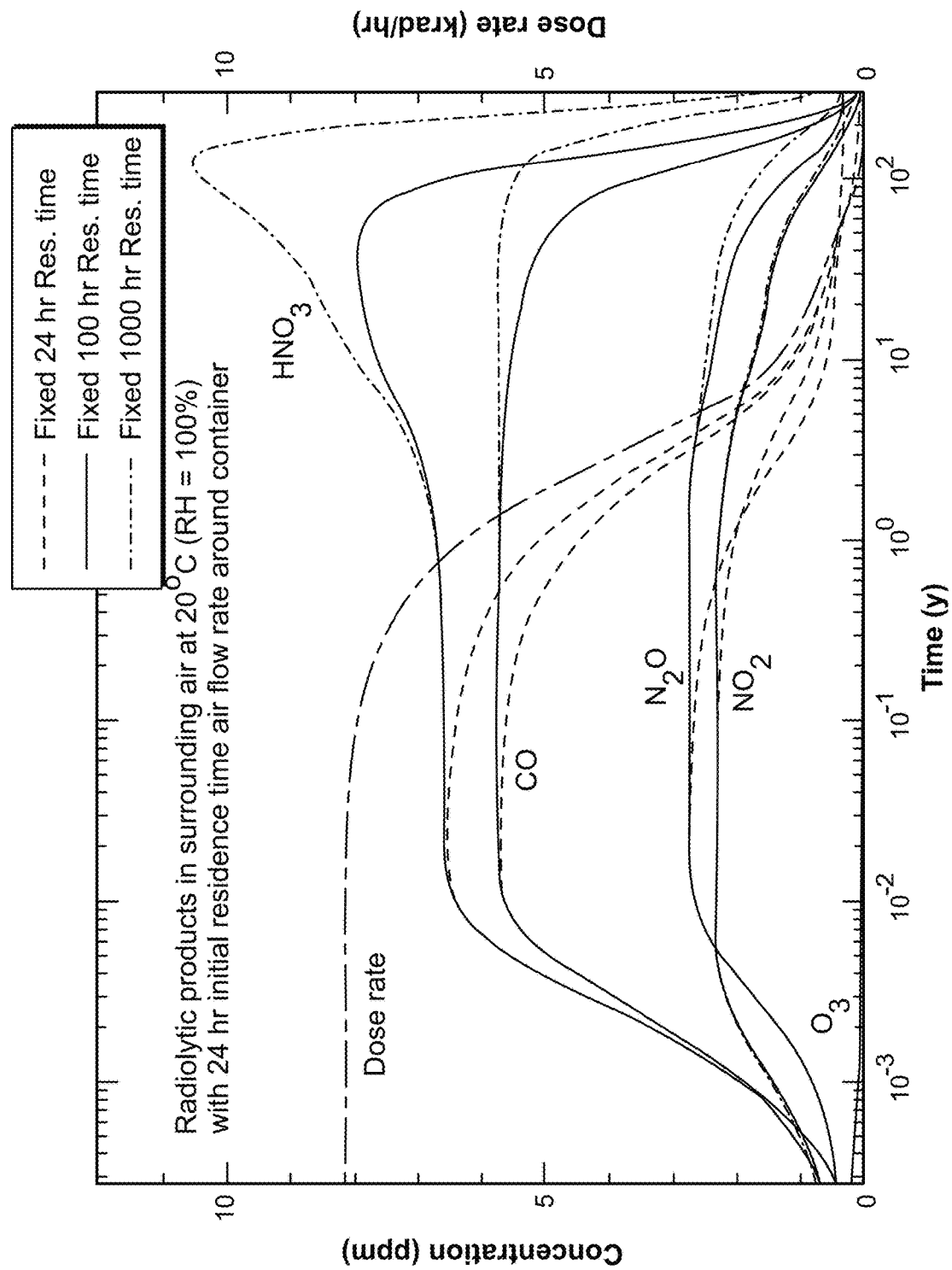
FIG. 3 shows model results of Wittman (Wittman, R., 2013, Radiolysis model sensitivity for a Used Fuel Storage Canister, Pacific Northwest National Laboratories PNNL-22773, 48p.) for radiolysis of air flowing past dry storage casks with a 24 hr residence time.

The ordinary differential equations take the form $$\frac{d[A_i]}{dt} + \frac{R}{V}([A_i] - [A_i]_0) = \dot{d}\sum_{g=1}^{N_g} G_i^{(0)} w_g [A_g] + \sum_{r=1}^{N_r} k_{ir} \prod_{j_r=1}^{n_r} [A_{j_r}]^{O_{ji}}$$

where the second term on the left-hand side involves R/V, which is the inverse residence time of continuously flowing reactor feed. The first term on the left-hand side includes radiolysis rates with dose d and radiolytic yields G for the various species, and the last term include mass action kinetics for reaction rates of bimolecular and termolecular reactions. An application of Wittman's (2013) (Wittman, R., 2013, Radiolysis model sensitivity for a Used Fuel Storage Canister, Pacific Northwest National Laboratories PNNL-22773, 48p.) model to radiolysis of air around a spent fuel canister is shown in FIG. 3, which shows a decline in dose rate over five hundred years, and the corresponding change in air chemistry, with different assumptions about the residence time of the surrounding air.

Figures 4A, 4B:
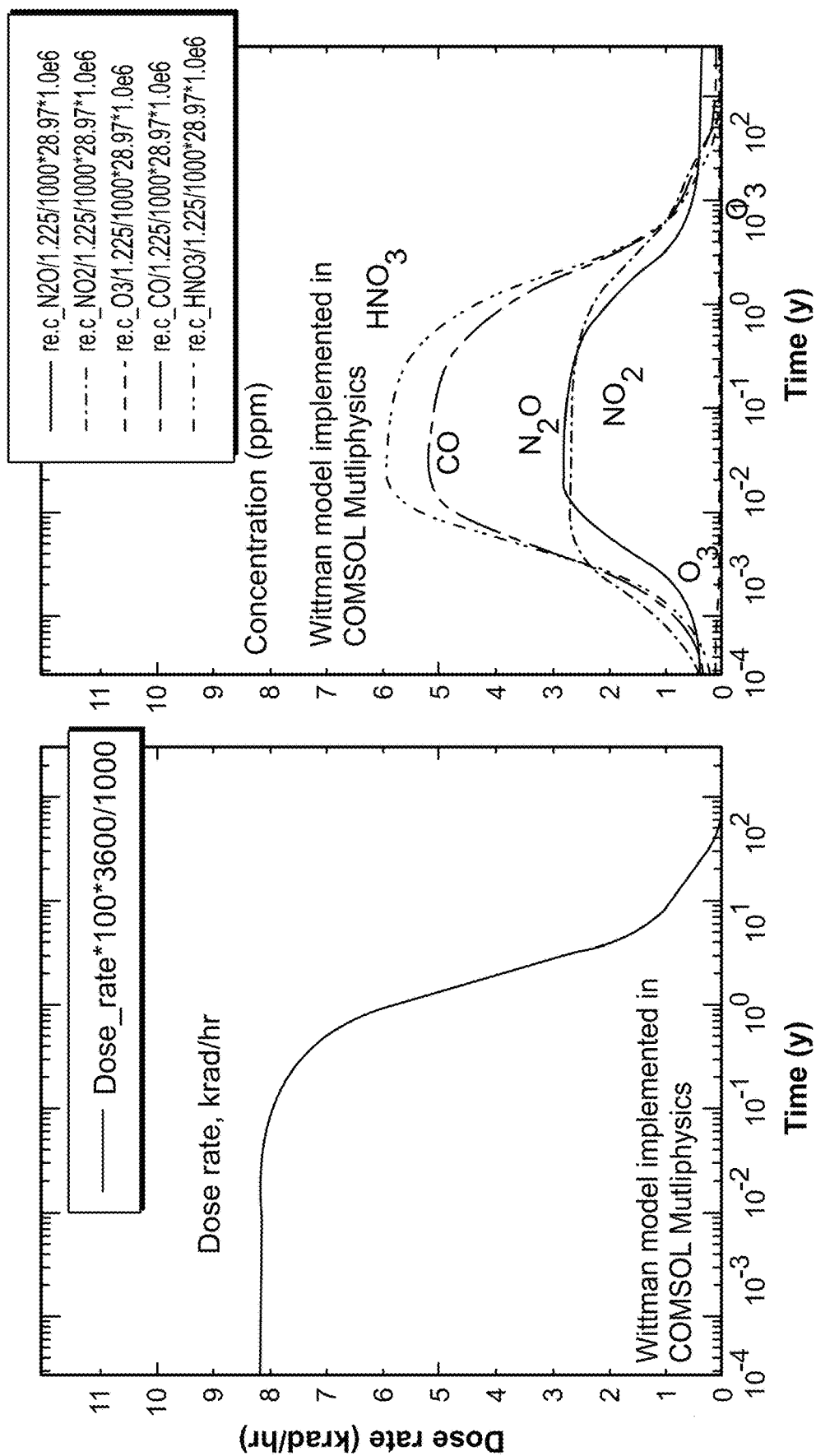
FIG. 4A shows results of COMSOL™ model showing model verification by comparison to results of Wittman (Wittman, R., 2013, Radiolysis model sensitivity for a Used Fuel Storage Canister, Pacific Northwest National Laboratories PNNL-22773, 48p.) given in FIG. 3. A. Dose rate same as curve in FIG. 3.
FIG. 4B shows concentrations of air radiolytic products, which exactly match the results of Wittman (Wittman, R., 2013, Radiolysis model sensitivity for a Used Fuel Storage Canister, Pacific Northwest National Laboratories PNNL-22773, 48p.).
Figures 5A, 5B, 5C:
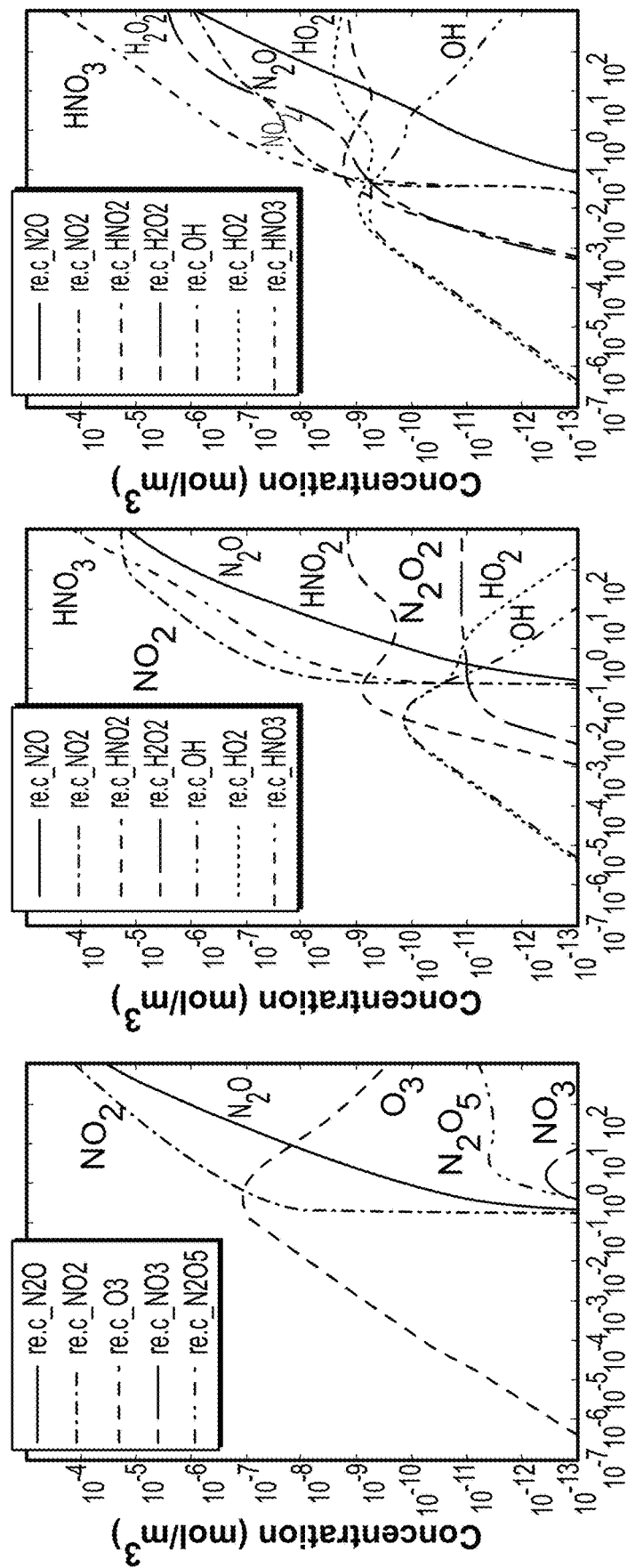
FIG. 5A shows results of COMSOL™ humid air radiolysis model according to an embodiment of this disclosure at zero RH (relative humidity).
FIG. 5B shows results of COMSOL™ humid air radiolysis model according to an embodiment of this disclosure at 10% RH. The presence of humidity results in different dominant chemical species compared to FIG. 5A.
FIG. 5C shows results of COMSOL™ humid air radiolysis model according to an embodiment of this disclosure at 85% RH. The high humidity results in different chemical species compared to FIGS. 5A and 5B.
Figures 5D, 5E, 5F:
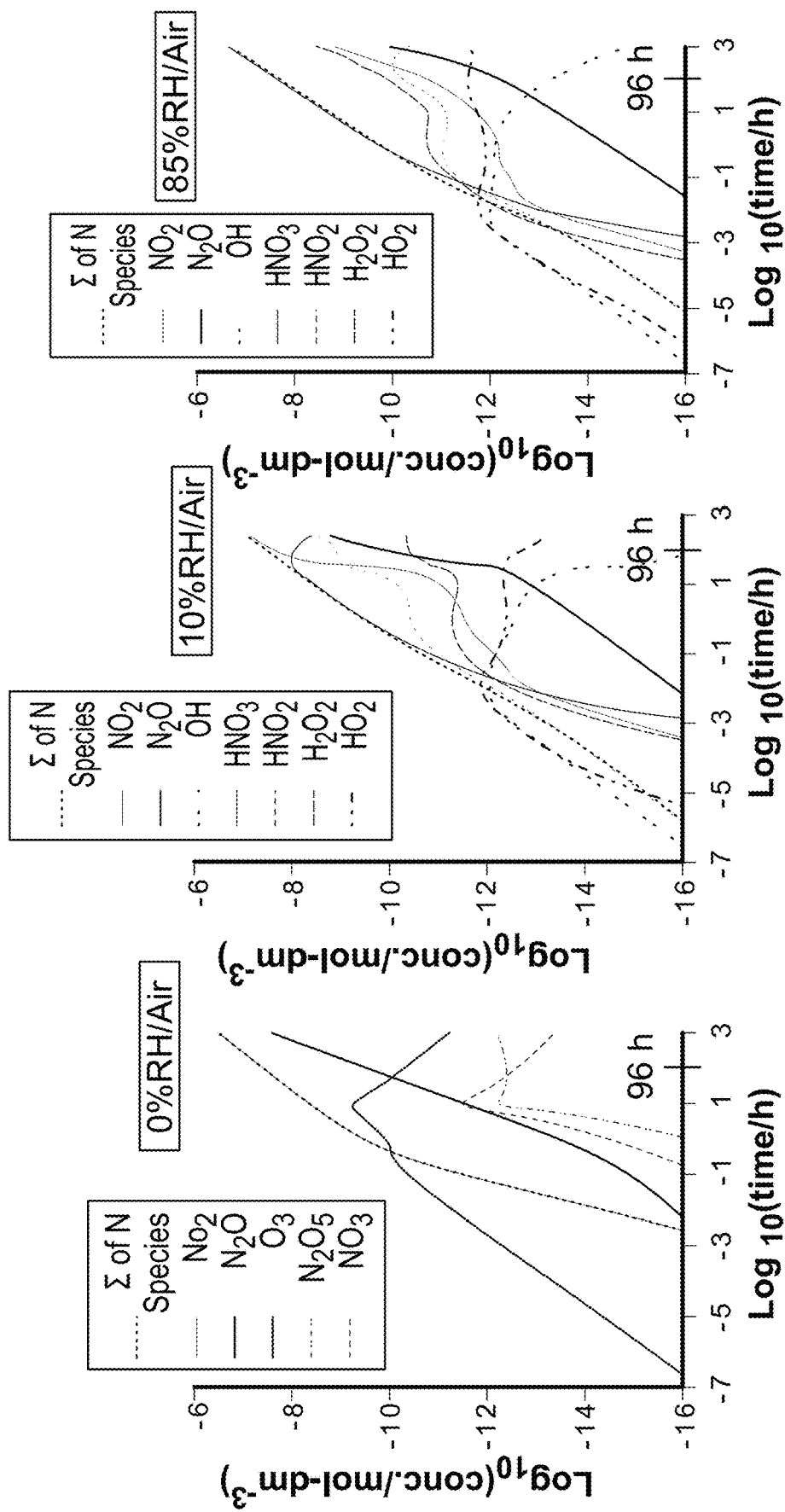
FIG. 5D shows results of FACSIMILE™ model according to an embodiment of this disclosure at 0% RH (relative humidity). Results are comparable to COMSOL™ model in FIG. 5A.
FIG. 5E shows results of FACSIMILE™ model according to an embodiment of this disclosure at 10% RH. Results are comparable to COMSOL™ model shown in FIG. 5B.
FIG. 5F shows results of FACSIMILE™ model according to an embodiment of this disclosure, at 85% RH. Results are comparable to COMSOL™ model in FIG. 5C.
Figure 6A:
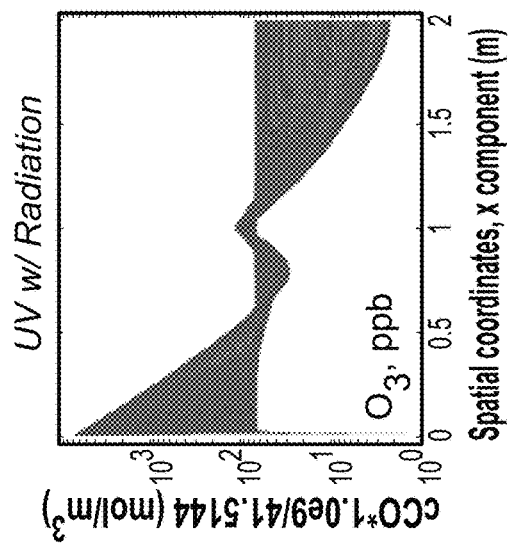
FIG. 6A shows simulations of the $O_x$—$OH_x$—$CO_x$—$NO_x$ air chemical system in a flow tube system with profiles shown at every time step for dark reaction with radiation.
Figure 6C:
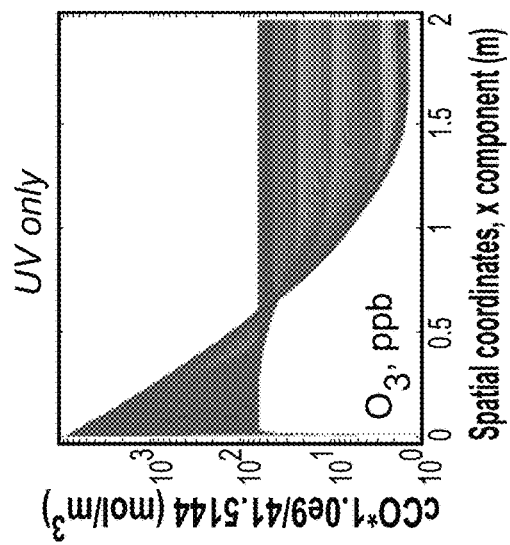
FIG. 6C shows simulations of the $O_x$—$OH_x$—$CO_x$—$NO_x$ chemical system in a flow tube system with profiles shown at every time step for UV only.
Figure 6E:
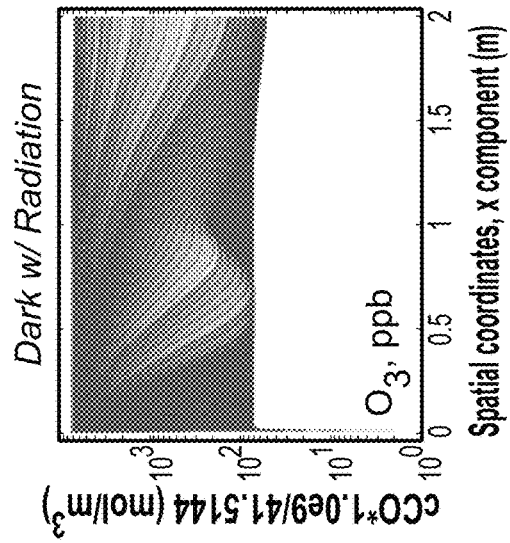
FIG. 6E shows simulations of the $O_x$—$OH_x$—$CO_x$—$NO_x$ chemical system in a flow tube system with profiles shown at every time step with UV and radiation.
Figure 6B:
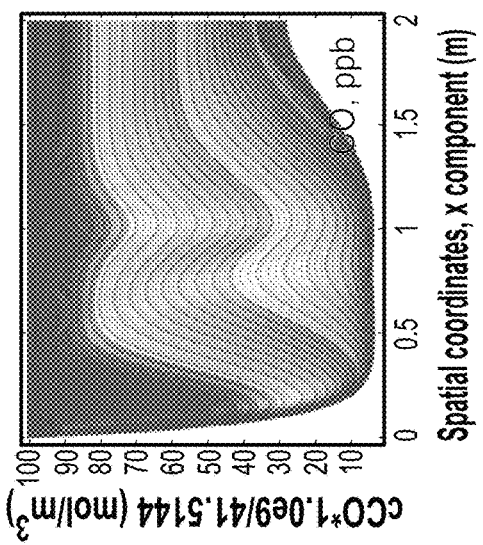
FIG. 6B shows simulations of the $O_x$—$OH_x$—$CO_x$—$NO_x$ chemical system in a flow tube system with profiles shown at every time step for dark reaction with radiation.
Figure 6D:
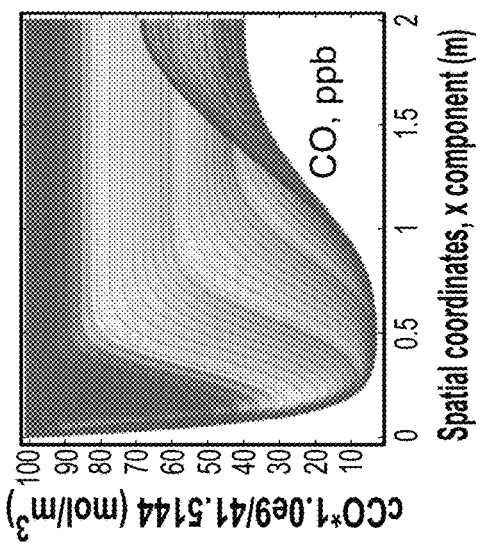
FIG. 6D shows simulations of the $O_x$—$OH_x$—$CO_x$—$NO_x$ chemical system in a flow tube system with profiles shown at every time step for UV only.
Figure 6F:
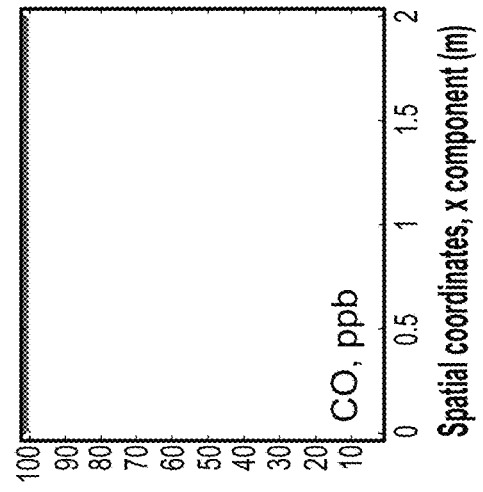
FIG. 6F shows simulations of the $O_x$—$OH_x$—$CO_x$—$NO_x$ chemical system in a flow tube system with profiles shown at every time step with UV and radiation.

The Wittman model was adapted into COMSOL™ and as a verification exercise, we duplicate one of his model runs from FIG. 3, below in FIG. 4. In other embodiments, another partial differential equation solver software may be used. The results are an exact match. As a further test of the COMSOL™ model to capture the desired behaviors, we compare our model runs to those of Morco (2020) (Morco, R. P., 2020, Gamma-Radiolysis kinetics and its role in the overall dynamics of materials degradation. Ph.D. Thesis, The University of Western Ontario, 250 p.; FACSIMILE™ Model found at https://www.mcpa-software.com/radiolysis-model, accessed Nov. 7, 2021) examining gamma radiolysis of humid air, at 75° C. and a dose rate of 1 Gy/h (FIGS. 5A-5F) using the radiolysis code FACSIMILE™. The COMSOL™ model does a good job reproducing the changing speciation at increasing humidity (from 0, 10, and 85% relative humidity) and a reasonable job at matching the concentrations. This suggests the adapted COMSOL™ model is well adapted to describe humid air radiolysis at a range of temperature, radiation, and humidity conditions.

For our chemosensor development, we are interested in coupling the above chemical and radiolytic kinetics with photolytic kinetics as many of the gas-phase oscillatory systems investigated in atmospheric sciences are driven by UV photolysis. To the Wittman-verified COMSOL™ model, 20 photolytic reaction rates were added as given in the Burkholder et al. (2021) (Burkholder, J. B., Sander, S. P., Abbatt, J., Barker, J. R., Huie, R. E., Kolb, C. E., Kurylo, M. J., Orkin, V. L., Wilmouth, D. M., and Wine, P. H., 2015, Chemical Kinetics and Photochemical Data for Use in Atmospheric Studies, Evaluation No. 18, JPL Publication 15-10, Jet Propulsion Laboratory, Pasadena, accessed Nov. 1, 2021, http://jpldataeval.jpl.nasa.gov) compilation where the rates are given by $$J_i = \int_{\lambda_1}^{\lambda_2} \phi_i(\lambda)\sigma_i(\lambda)I(\lambda)d\lambda$$

where the right-hand side is the product of wavelength-dependent quantum yield, species absorption cross-section, and photon flux or intensity. The wavelength dependence and the varying intensity of UV sources should allow a wide range of "tuning" the resulting nonlinear rates, and it follows the oscillatory behavior, chemical wave behavior, and response when coupled to radiolysis. This allows an ability to tune a chemical wave chemosensor to be able to discern between sources of radiolytic yield.

To demonstrate the occurrence and sensitivity of this gas-phase system to the development of spatially propagating chemical waves, we couple the CSTR system to a "flow tube", wherein the reactor effluent is fed into a 6" square cross-section fused-quartz or Teflon tube that is approximately 2 m in length. The flow tube allows demonstration of chemical wave behavior in a quasi-one-dimensional spatial format (i.e., 1D wave propagation and flow). The experimental design here includes a surrogate radiation source to be located at the center of the tube, utilizing an $O_3$—$NO_x$ source at the tube longitudinal center, to demonstrate the wave behavior as perturbed by a radiation source. The choice of fused quartz glass or Teflon is associated with the particular UV transmissivity that is required to excite the required photolytic reactions in the nonlinear chemical wave reaction network. Both quartz and TFE Teflon are used in atmospheric reaction kinetic studies involving UV photolysis.

A 1-D model of this system shows the expected behavior under different environmental conditions (FIG. 6). The "dark" condition just involves bimolecular and termolecular reactions, the UV condition includes these plus photolytic reactions sensitive to the precise UV wavelength, and the UV with-radiation condition includes all of the above plus radiolysis kinetics sensitive to the dose rate and precise radionuclide(s). The dark example shows ozone concentration slowly increasing with time with successive diffusion-dispersion profiles. The UV only and UV-with-radiation examples display chemical wave behavior, propagating from left to right in the successive time profiles. The UV plus radiation example shows the influence of the point source of radiation (as shown in FIGS. 6A-6F), and how the information contained in the chemical wave is transmitted to the tube effluent side by the propagating chemical wave.

Sensing in Liquid Phase Systems with Chemical Waves

In liquid phase systems, chemical wave systems can be used to: interrogate the liquid-filled disturbed rock zones around borehole excavations into crystalline rock for contaminant migration; interrogate boreholes directly and perform material accountancy (i.e., to quantify that the expected amount of material is in place); and detect and signal that the system had been intruded in some way. Here, a "push-pull" injection-extraction method is drawn from many environmental remediation technologies. Oscillatory chemical systems with known chemical wave behaviors are injected (pushed) into a region of interest, held there for a specified time, and then extracted (pulled) for analysis. Differences in the wave behavior between the injected and extracted samples are interrogated. This approach is similar in reaction kinetics, sensing, and analysis as described above for gas-phase systems.

The Belousov-Zhabotinsky (BZ) liquid phase chemical wave system has demonstrated chemical wave behavior using a variant of the BZ reaction in small glass micromodels. For our purposes, a variant of the original BZ reaction is used as it does not off-gas $CO_2$ and maintains a single aqueous phase system during operation. The oscillatory reaction as simulated by computer solution of the reaction equations involves bromate and iron species as well as an organic substrate.

Proposed Experimental Procedure

This experimental design is meant to test liquid-phase chemical wave systems used to interrogate disturbed rock zones surrounding excavated underground repositories or deep boreholes in crystalline rock, namely regions that are difficult to access for other sensing types. This interrogation is to be developed to: assess contaminant migration; perform material accountancy (i.e., to quantify that the expected amount of material is in place); and detect and signal that the fractured rock system had been intruded as based on changes in the character of the fractured system or porous media. The notion here is that of a "push-pull" injection-extraction method, drawn from many environmental remediation technologies, that can be utilized here to access porous or fractured regions of relatively impermeable rock or engineered clay- or concrete barriers. Oscillatory chemical systems with known chemical wave behaviors are injected (pushed) into a region of interest, held there for a specified time, and then extracted (pulled) for analysis. Differences in the wave behavior between the injected and extracted samples are interpreted for point or spatial distributed perturbations that alter the wave behavior.

Figure 7A:
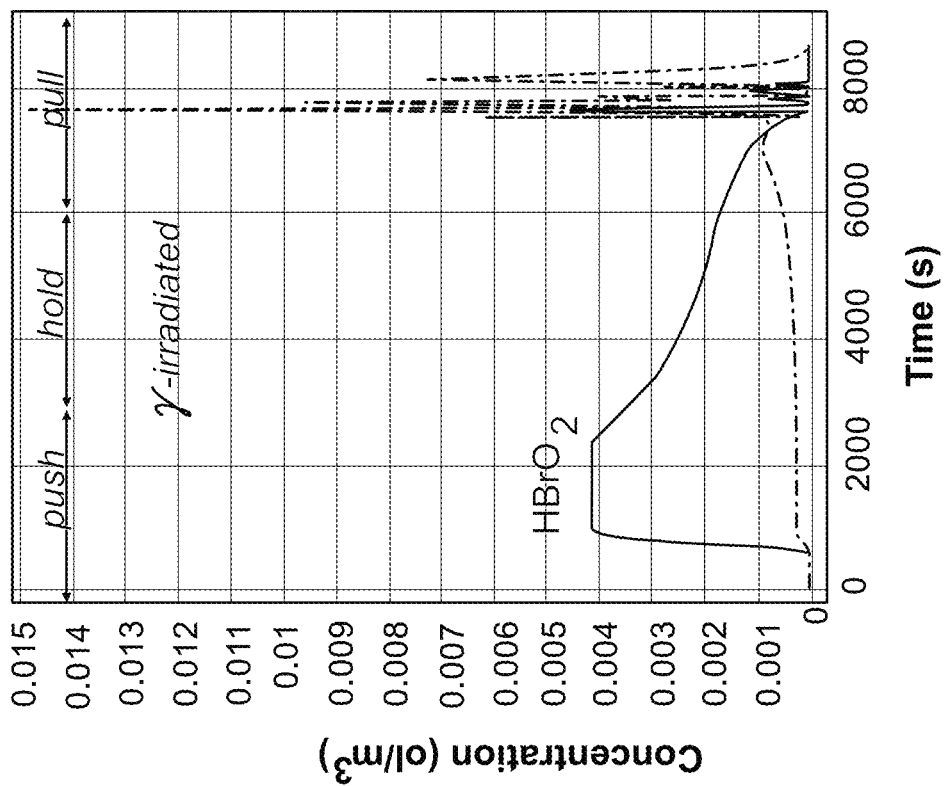
FIG. 7A shows simulations of BZ chemical wave behavior in a 0.5-meter radial-dimension domain, showing development of chemical wave behavior at a monitoring port located at 0.1 m from the central injection location.
Figure 7B:
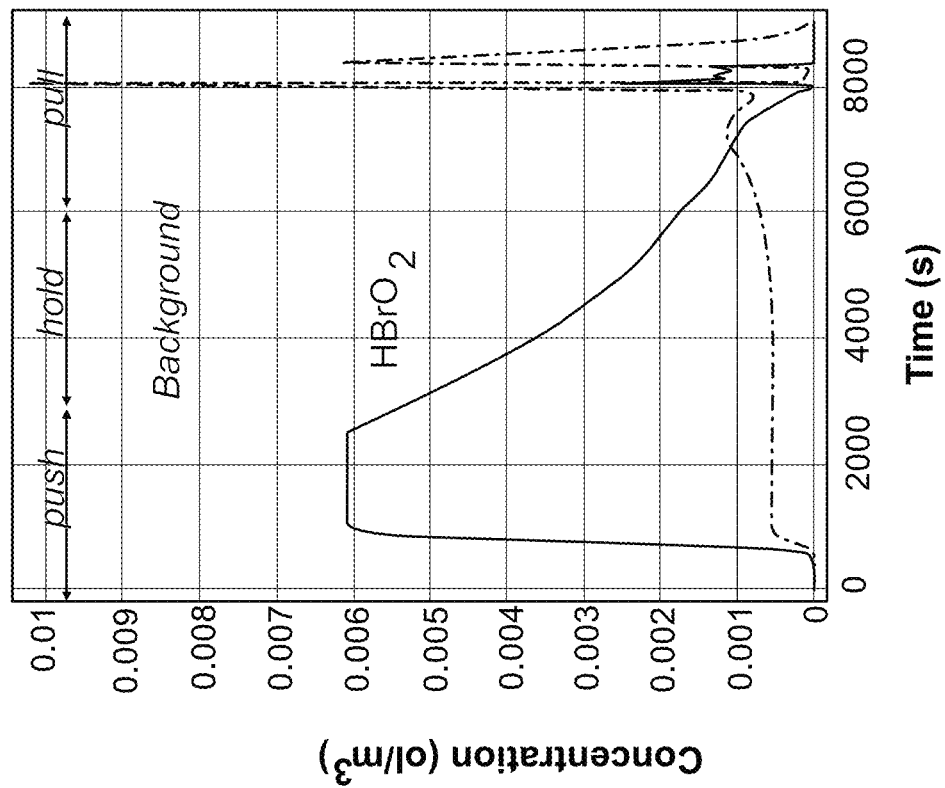
FIG. 7B shows simulations of BZ chemical wave behavior in a 0.5-meter radial-dimension domain, showing BZ behavior during the same push-hold-pull behavior as FIG. 7A but perturbed by gamma radiation. In this way, the model simulates the injection of the Chemosensor system into a porous media, and the extraction of the system for analysis.

An example of push-hold-pull methods of injection and extraction is shown in FIG. 7. In this case, using aqueous phase chemical wave systems, we first inject a chemical mixture of bromate and iron species for 3,000 s, hold the material in place for 3,000 s (wherein the oscillatory behavior commences), and then extract the solution back for 3,000 s. For modeling purposes, a porous media with porosity of 0.35 and a permeability of 1.0E-12 $m^2$ was assumed, and standard water properties at 25° C. and 1 atm fluid pressure. In FIG. 7A, a push-pull example is shown with 3,000 s for each phase, injecting a suite of BZ chemistry into a central "borehole" for 3,000 s, pausing for 3,000 s for wave development, and then extraction for 3000 s, examining the chemical profiles at a location 0.1 m from the central borehole. We compare the BZ behavior of two species in a "background" setting (FIG. 7A) to a BZ system exposed to gamma-radiation, coupled to radiolytic effects via water radiolysis, in FIG. 7B right panel. This shows the background oscillations of a bromate and a ferrous iron species, and the modeled effect of exposure to gamma radiation. The differences underscore the potential of this BZ system as a chemosensor for examining a solid rock body surrounding an excavated or borehole zone for radioactive contaminants.

Previous art gives details on the BZ reactions and other classes of liquid phase chemical wave systems such as pH oscillators, along with chemical constituents of interest that are involved in the nonlinear chemical reaction networks and monitoring methods such as ion specific electrodes or redox probes. In an embodiment, we propose the application for monitoring using non-linear reactions that exhibit behaviors like those of BZ, pH oscillators (Orban, M., Kurin-Csorgei, K., and Epstein, I. R., 2015, pH-regulated chemical oscillators, Accounts Chem. Res. 48, 593-601), or similar chemical wave systems and commensurate liquid solute/species measurement systems (e.g., ion specific electrodes and/or redox probes; liquid chromatography, inductively coupled plasma-atomic emission spectrometry, flame emission or other laboratory methods for collected samples) in the push-pull scenario. The application includes analysis of chemical wave behavior for appropriate kinetics, stoichiometry, and feedbacks to produce desired monitoring of chemical wave behavior including signal amplification and chemical wave information transmission, and thus our invention applies to the vast array of liquid chemical wave reaction networks that exhibit the desired behaviors.

For our lab testing, a variant of the original Belousov-Zhabotinsky (BZ) reaction due to Szalai et al. (2003) (Szalai, I., Kurin-Csorgei, K., and Orban, M., 2002, Mechanistic studies on the bromate-1,4-cyclohexanedione-ferroin oscillatory system. Phys. Chem. Chem. Phys. 4, 1271-1275) is used, which is useful for the aqueous chemosensor system as it does not off-gas $CO_2$ and maintains a single aqueous phase system during operation. The oscillatory reaction is quite complex, with 40 or so steps involving bromate and iron species as well as an organic substrate. Our experimental design uses a Hele Shaw cell involving two parallel plates with a small gap in between that is either liquid-filled or filled with a porous media that could include a fracture network, which has been used previously for BZ reaction studies (Vodopivec, 2020) (Vodopivec, D. M. E., 2020, Hydrodynamic instabilities coupled with complex chemical reactions: Control, characterization, and their modeling. Ph.D. Dissertation, Universidad de Santiago de Compostela, 248.).

The invention being thus described, it will be obvious that the same may be varied in many ways. Such variations are not to be regarded as a departure from the spirit and scope of the invention, and all such modifications as would be obvious to one skilled in the art are intended to be included within the scope of the appended claims. It is intended that the scope of the invention be defined by the claims appended hereto. The entire disclosures of all references, applications, patents and publications cited above are hereby incorporated by reference.

In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A monitoring method, comprising:
   introducing autocatalytic chemical wave compounds into an area of interest for a first period of time;
   monitoring the chemical wave compound concentrations at one or more detection sites to create a chemical wave profile over the first period of time; and
   analyzing the monitored chemical wave profiles using inverse modeling and parameter estimation to determine if a perturbation has taken place in the second period of time by a perturbation source;
      wherein the measured chemical wave is used to estimate underlying system state parameters that affect the chemical waves, including substances such as radiation by-products and their locations, type, and strength.

2. The method of claim 1, wherein the perturbation source is a target substance.

3. The method of claim 1, wherein the underlying system parameters or variables are selected from the group consisting of radiation by-products, radiation by-product locations, radiation by-product types and radiation by-product strengths, and chemicals released or deposited during or by seal breaching or other residues.

4. The method of claim 1, further comprising:
   introducing the autocatalytic chemical wave compounds into the area of interest for a pre-period of time prior to the first period of time;
   monitoring the chemical wave compound concentrations introduced during the pre-period of time at one or more detection sites to create a baseline chemical wave profile over the pre-period of time;
   introducing the autocatalytic chemical wave compounds into the area of interest for a second period of time;
   monitoring the chemical wave compound concentrations at one or more detection sites for a second period of time to create a monitored chemical wave profile; and
   analyzing the baseline and monitored chemical wave profiles to determine if a perturbation has taken place in the second period of time.

5. The method of claim 1, further comprising:
   determining the type of perturbation.

6. The method of claim 5, wherein the type of perturbation is selected from the group consisting of removal of a radiation source, radiation leakage, repositioning or removal of containers or other items in the system, chemicals released by seal breaching or other residues perturbed by unauthorized access, and intrusion into the system that changes geometric or chemical features of the system.

7. The method of claim 1, wherein the perturbation indicates a change in a radiological condition.

8. The method of claim 1, wherein the baseline and monitored chemical wave profiles are analyzed by chemical species detection.

9. The method of claim 8, wherein chemical species detection is performed by a detection method selected from the group consisting essentially of laser detection, absorption detection, and vibrational spectroscopy, and by devices that emit electromagnetic radiation that is absorbed by chemical species of interest as monitored by photo-detection.

10. The method of claim 9, wherein the devices are selected from the group consisting essentially of photo-diodes, a charged-coupled device (CCD) camera, lab-based chromatography, spectroscopic devices and mass spectrometers.

11. The method of claim 1, wherein the detection includes amplification by the chemical wave systems through which non-linear feedback reactions that lead to chemical oscillations, enhancements, or unbounded growth within a range in small chemical signals or concentrations that are detected and at greater level than a non-amplified level than the target monitored substance thereby causing an amplification and improved detection of the target substance or perturbing source.

12. The method of claim 1, wherein the chemical wave profile detection uses ion specific electrodes in field or experiment settings or lab-based measurements for collected samples.

13. The method of claim 12, wherein the lab-based measurements are performed via a technique selected from the group consisting essentially of liquid chromatography, inductively coupled plasma-atomic emission spectrometry, and flame emission.

* * * * *